United States Patent
Tabary et al.

(10) Patent No.: US 11,261,445 B2
(45) Date of Patent: Mar. 1, 2022

(54) COMBINATION TREATMENT FOR CYSTIC FIBROSIS

(71) Applicants: INSERM (Institut National de la Santé et de la Recherche Médicale), Paris (FR); Sorbonne Université, Paris (FR); Assistance Publique-Hôpitaux de Paris (APHP), Paris (FR)

(72) Inventors: Olivier Tabary, Paris (FR); Florence Sonneville, Paris (FR); Harriet Corvol, Paris (FR)

(73) Assignees: INSERM (INSTITUT NATIONAL DE LA SANTE ET DE LA RECHERCHE MEDICALE), Paris (FR); SORBONNE UNIVERSITE, Paris (FR); ASSISTANCE PUBLIQUE-HOPITAUX DE PARIS (APHP), Paris (FR)

( * ) Notice: Subject to any disclaimer, the term of this patent is extended or adjusted under 35 U.S.C. 154(b) by 21 days.

(21) Appl. No.: 16/756,917

(22) PCT Filed: Oct. 16, 2018

(86) PCT No.: PCT/EP2018/078283
§ 371 (c)(1),
(2) Date: Apr. 17, 2020

(87) PCT Pub. No.: WO2019/076919
PCT Pub. Date: Apr. 25, 2019

(65) Prior Publication Data
US 2021/0189390 A1    Jun. 24, 2021

(30) Foreign Application Priority Data
Oct. 17, 2017 (EP) .................... 17306406

(51) Int. Cl.
| | |
|---|---|
| C07H 21/04 | (2006.01) |
| A61K 48/00 | (2006.01) |
| C12N 15/113 | (2010.01) |
| A61P 11/00 | (2006.01) |
| A61K 9/00 | (2006.01) |
| A61K 9/20 | (2006.01) |
| A61K 31/443 | (2006.01) |
| A61K 31/47 | (2006.01) |

(52) U.S. Cl.
CPC .......... *C12N 15/113* (2013.01); *A61K 9/0053* (2013.01); *A61K 9/20* (2013.01); *A61K 31/443* (2013.01); *A61K 31/47* (2013.01); *A61P 11/00* (2018.01); *C12N 2310/141* (2013.01); *C12N 2310/3231* (2013.01)

(58) Field of Classification Search
CPC ......................... C12N 15/113; C12N 2310/11
See application file for complete search history.

(56) References Cited

FOREIGN PATENT DOCUMENTS

| WO | 2014/011053 A1 | 1/2014 |
|---|---|---|
| WO | 2017/005646 A1 | 1/2017 |
| WO | 2017/006145 A1 | 1/2017 |
| WO | 2017/118915 A1 | 7/2017 |

OTHER PUBLICATIONS

Sonneville; "Régulation du canal chlorure ANO1 par les miARN et stratégie thérapeutique dans la mucoviscidose" retrieved from the internet: URL:https://tel.archives-ouvertes.fr/tel-01504599v2/document; Sep. 26, 2016, pp. 36-38, 58, 59, 114-116, 124, 177, 178.
Sonneville et al.; "MicroRNA-9 downregulates the ANO1 chloride channel and contributes to cystic fibrosis lung pathology"; Nature Communications, vol. 8, No. 1, Sep. 27, 2017, the entire document.
Schneider et al.; "Can Cystic Fibrosis Patients Finally Catch a Breath With Lumacaftor/Ivacaftor?" Clinical Pharmacology and Therapeutics, vol. 101, No. 2, 2016, pp. 130-141.
Brodlie et al.; "Targeted therapies to improve CFTR function in cystic fibrosis"; Genome Medicine, vol. 7, No. 1, Sep. 24, 2015, pp. 11-13.
Wainwright et al.; "Lumacaftor-Ivacaftor in Patients with Cystic Fibrosis Homozygous for Phe508del CFTR" New England Journal of Medicine, vol. 373, No. 3, Aug. 17, 2015, pp. 220-231.
Kuk et al.; "Lumacaftor and ivacaftor in the management of patients with cystic fibrosis: current evidence and future prospects"; Therapeutic Advances in Respiratory Diseases, vol. 9, No. 6, Sep. 28, 2015; pp. 313-326.

*Primary Examiner* — Amy H Bowman
(74) *Attorney, Agent, or Firm* — WC&F IP

(57) ABSTRACT

Cystic fibrosis (CF) is a genetic disease caused by mutations in the gene encoding the 5 CFTR Cl— channel and affects several organs, but the most severe consequences are observed in the lung. The inventors have now instigated the combination of Orkambi® and ANO1 TSB (SEQ ID NO:1) and show that said combination increases mucociliary clearance and chloride channel activity. Thus the combination represents an alternative treatment for CF subjects.

Figure 1:
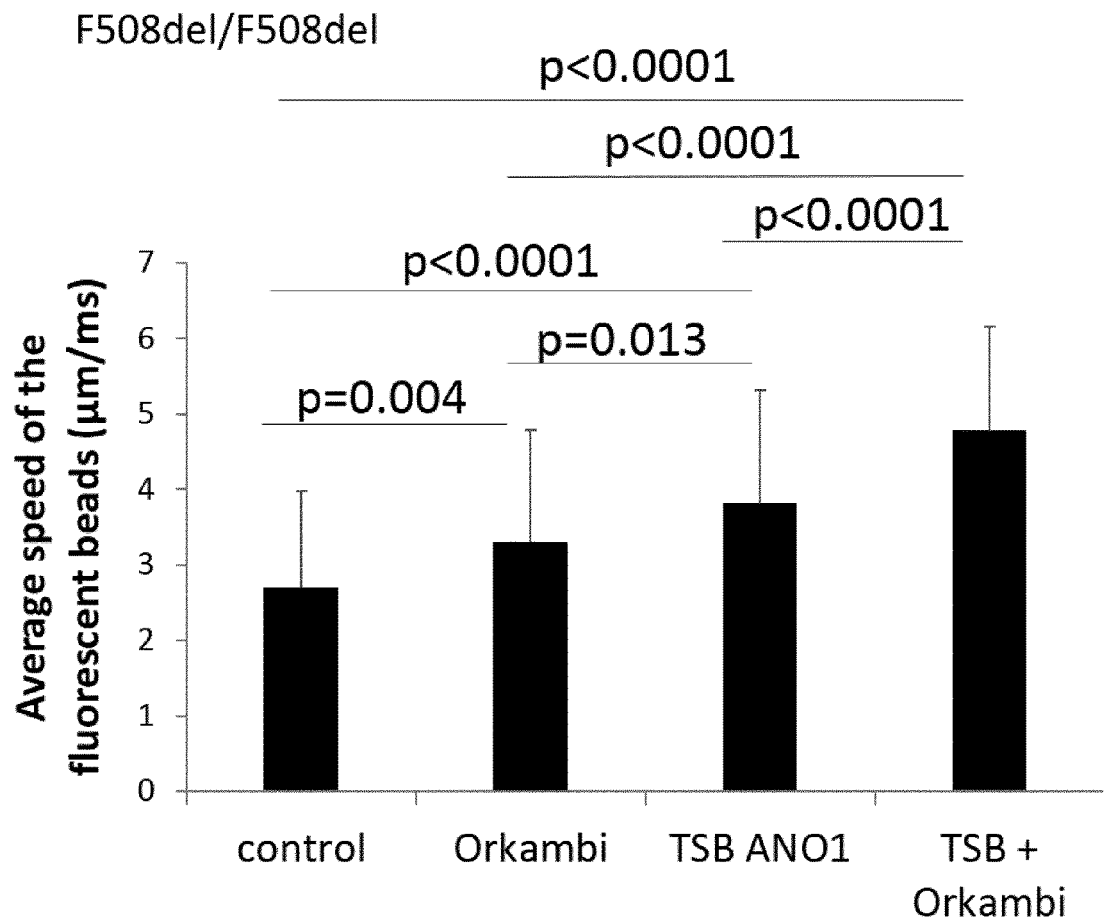

12 Claims, 4 Drawing Sheets
Specification includes a Sequence Listing.

COMBINATION TREATMENT FOR CYSTIC FIBROSIS

FIELD OF THE INVENTION

The present invention relates to combination treatment of cystic fibrosis.

BACKGROUND OF THE INVENTION

Cystic fibrosis (CF) is a genetic disease caused by mutations in the gene encoding the CFTR Cl— channel (Riordan, 2008). CF affects several organs, but the most severe consequences are observed in the lung. The pathogenesis of lung disease in CF is still not perfectly understood. The loss of CFTR channel function in CF favors the colonization of the airway surface by highly virulent bacteria. However, the mechanism by which this happens is still a matter of debate. CFTR channel activity is certainly an important contributor to mucociliary clearance. The fine balance between CFTR-dependent Cl— secretion and Na+ absorption through the ENaC channel controls the thickness of the periciliary fluid (PCF). In the absence of functional CFTR, fluid absorption prevails over secretion. This imbalance dehydrates the airway surface thereby impairing ciliary beating. Immobilized mucus then becomes a niche for bacterial survival and proliferation. Several strategies of treatment have been explored. For instance, in 2016, the Food and Drug Administration and the European Commission approved LUM/IVA (Orkambi®), a CFTR modulator that includes both a CFTR corrector and potentiator, for CF patients homozygous for the F508del CFTR mutation (Bulloch M N, Hanna C, Giovane R.vLumacaftor/ivacaftor, a novel agent for the treatment of cystic fibrosis patients who are homozygous for the F580del CFTR mutation. (Expert Rev Clin Pharmacol. 2017 October; 10(10):1055-1072). Recently, the use of a target site blocker targeting the seed region of miR-9 demonstrates the potential benefits of ANO1 therapy for the treatment of cystic fibrosis patients (WO2017006145 and Sonneville F, Ruffin M, Coraux C, et al. MicroRNA-9 downregulates the ANO1 chloride channel and contributes to cystic fibrosis lung pathology. Nature communications 2017; 8: 710).

SUMMARY OF THE INVENTION

The present invention relates to combination treatment of cystic fibrosis. In particular, the present invention is defined by the claims.

DETAILED DESCRIPTION OF THE INVENTION

The present invention relates to a method of treating cystic fibrosis in a subject in need thereof comprising administering to the subject a therapeutically effective combination of lumacaftor, ivacaftor and a nucleic acid molecule comprising the nucleic acid sequence

```
                                            (SEQ ID NO: 1)
                      TTTTCTCCGTCTTTGGGACCT.
```

As used herein, the term "subject" denotes a mammal. A subject according to the invention refers to any subject (preferably human) afflicted or at risk to be afflicted with cystic fibrosis. The method of the invention may be performed for any type of cystic fibrosis such as revised in the World Health Organisation Classification of cystic fibrosis and selected from the E84 group: mucoviscidosis, Cystic fibrosis with pulmonary manifestations, Cystic fibrosis with intestinal manifestations and Cystic fibrosis with other manifestations.

As used herein, the term "CFTR protein" refers to the CFTR protein of 1480 amino acids also called Cystic Fibrosis Transmembrane Regulator. The CFTR protein is a chloride (Cl—) channel and is found in the membranes of intestinal and respiratory mucosa. The CFTR protein is represented by the NCBI reference sequence: P13569.3 (SEQ: ID NO: 2)

```
SEQ ID NO: 2:
   1 mqrsplekas vvsklffswt rpilrkgyrq rlelsdiyqi psvdsadnls eklerewdre 61 laskknpkli nalrrcffwr fmfygiflyl gevtkavqpl llgriiasyd pdnkeersia 121 iylgiglcll fivrtlllhp aifglhhigm qmriamfsli ykktlklssr vldkisigql 181 vsllsnnlnk fdeglalahf vwiaplqval lmgliwellq asafcglgfl ivlalfqagl 241 grmmmkyrdq ragkiserlv itsemieniq svkaycweea mekmienlrq telkltrkaa 301 yvryfnssaf ffsgffvvfl sylpyalikg illrkiftti sfcivlrmav trqfpwavqt 361 wydslgaink iqdflqkqey ktleynittt evvmenvtaf weegfgelfe kakqnnnnrk 421 tsngddslff snfsllgtpv lkdinfkier gqllavagst gagktsllmv imgelepseg 481 kikhsgrisf csqfswimpg tikeniifgv sydeyryrsv ikacqleedi skfaekdniv 541 lgeggitlsg gqrarislar avykdadlyl ldspfgyldv ltekeifesc vcklmanktr 601 ilvtskmehl kkadkililh egssyfygtf selqnlqpdf ssklmgcdsf dqfsaerrns 661 iltetlhrfs legdapvswt etkkqsfkqt gefgekrkns ilnpinsirk fsivqktplq 721 mngieedsde plerrlslvp dseqgeailp risvistgpt lqarrrqsvl nlmthsvnqg 781 qnihrkttas trkvslapqa niteldiysr rlsqetglei seeineedlk ecffddmesi 841 pavttwntyl ryitvhksli fvliwclvif laevaaslvv lwllgntplq dkgnsthsrn
```

```
 901 nsyaviitst ssyyvfyiyv gvadtllamg ffrglplvht litvskilhh kmlhsvlqap 961 mstlntlkag gilnrfskdi ailddllplt ifdfiqllli vigaiavvav lqpyifvatv 1021 pvivafimlr ayflqtsqql kqlesegrsp ifthlvtslk glwtlrafgr qpyfetlfhk 1081 alnlhtanwf lylstlrwfq mriemifvif fiavtfisil ttgegegrvg iiltlamnim 1141 stlqwavnss idvdslmrsv srvfkfidmp tegkptkstk pykngqlskv miienshvkk 1201 ddiwpsggqm tvkdltakyt eggnaileni sfsispgqry gllgrtgsgk stllsaflrl 1261 lntegeiqid gvswdsitlq qwrkafgvip qkvflfsgtf rknldpyeqw sdqeiwkvad 1321 evglrsvieq fpgkldfvlv dggcvlshgh kqlmclarsv lskakillld epsahldpvt 1381 yqiirrtlkq afadctvilc ehrieamlec qqflvieenk vrqydsiqkl lnerslfrqa 1441 ispsdrvklf phrnsskcks kpqiaalkee teeevqdtrl
```

As used herein, the term "CFTR gene" refers to the CFTR gene which is located on chromosome 7 and which may be found in NCBI GenBank locus AC000111 and AC000061, the contents of which are incorporated herein in their entirety by reference. The cDNA for the CFTR gene is found in Audrezet et al., Hum. Mutat. (2004) 23 (4), 343-357. A nucleic acid sequence for human CFTR is represented by SEQ ID NO: 3.

```
                (NCBI Reference Sequence: NM_000492.3)
                                                        SEQ ID NO: 3
   1 aattggaagc aaatgacatc acagcaggtc agagaaaaag ggttgagcgg caggcaccca 61 gagtagtagg tctttggcat taggagcttg agcccagacg gccctagcag ggaccccagc 121 gcccgagaga ccatgcagag gtcgcctctg gaaaaggcca gcgttgtctc caaacttttt 181 ttcagctgga ccagaccaat tttgaggaaa ggatacagac agcgcctgga attgtcagac 241 atataccaaa tccttctgt tgattctgct gacaatctat ctgaaaaatt ggaaagagaa 301 tgggatagag agctggcttc aaagaaaaat cctaaactca ttaatgccct tcggcgatgt 361 tttttctgga gatttatgtt ctatggaatc tttttatatt taggggaagt caccaaagca 421 gtacagcctc tcttactggg aagaatcata gcttcctatg acccggataa caaggaggaa 481 cgctctatcg cgatttatct aggcataggc ttatgccttc tctttattgt gaggacactg 541 ctcctacacc cagccatttt tggccttcat cacattggaa tgcagatgag aatagctatg 601 tttagtttga tttataagaa gactttaaag ctgtcaagcc gtgttctaga taaataagt 661 attggacaac ttgttagtct cctttccaac aacctgaaca aatttgatga aggacttgca 721 ttggcacatt tcgtgtggat cgctcctttg caagtgcac tcctcatggg gctaatctgg 781 gagttgttac aggcgtctgc cttctgtgga cttggtttcc tgatagtcct tgccctttt 841 caggctgggc tagggagaat gatgatgaag tacagagatc agagagctgg gaagatcagt 901 gaaagacttg tgattacctc agaaatgatt gaaaatatcc aatctgttaa ggcatactgc 961 tgggaagaag caatggaaaa aatgattgaa acttaagac aaacagaact gaaactgact 1021 cggaaggcag cctatgtgag atacttcaat agctcagcct tcttcttctc agggttcttt 1081 gtggtgtttt tatctgtgct tccctatgca ctaatcaaag gaatcatcct ccggaaaata 1141 ttcaccacca tctcattctg cattgttctg cgcatggcgg tcactcggca atttccctgg 1201 gctgtacaaa catggtatga ctctcttgga gcaataaaca aaatacagga tttcttacaa 1261 aagcaagaat ataagacatt ggaatataac ttaacgacta cagaagtagt gatggagaat 1321 gtaacagcct tctgggagga gggatttggg gaattatttg agaaagcaaa acaaaacaat 1381 aacaatagaa aaacttctaa tggtgatgac agcctcttct tcagtaattt ctcacttctt 1441 ggtactcctg tcctgaaaga tattaatttc aagatagaaa gaggacagtt gttggcggtt
```

-continued

```
1501 gctggatcca ctggagcagg caagacttca cttctaatgg tgattatggg agaactggag
1561 ccttcagagg gtaaaattaa gcacagtgga agaatttcat tctgttctca gttttcctgg
1621 attatgcctg gcaccattaa agaaaatatc atctttggtg tttcctatga tgaatataga
1681 tacagaagcg tcatcaaagc atgccaacta gaagaggaca tctccaagtt tgcagagaaa
1741 gacaatatag ttcttggaga aggtggaatc acactgagtg gaggtcaacg agcaagaatt
1801 tctttagcaa gagcagtata caaagatgct gatttgtatt tattagactc tccttttgga
1861 tacctagatg ttttaacaga aaagaaata tttgaaagct gtgtctgtaa actgatggct
1921 aacaaaacta ggattttggt cacttctaaa atggaacatt taaagaaagc tgacaaaata
1981 ttaattttgc atgaaggtag cagctatttt tatgggacat tttcagaact ccaaaatcta
2041 cagccagact ttagctcaaa actcatggga tgtgattctt tcgaccaatt tagtgcagaa
2101 agaagaaatt caatcctaac tgagaccttat caccgtttct cattagaagg atgctcct
2161 gtctcctgga cagaaacaaa aaaacaatct tttaaacaga ctggagagtt tggggaaaaa
2221 aggaagaatt ctattctcaa tccaatcaac tctatacgaa aattttccat tgtgcaaaag
2281 actcccttac aaatgaatgg catcgaagag gattctgatg agcctttaga gagaaggctg
2341 tccttagtac cagattctga gcaggagag gcgatactgc ctcgcatcag cgtgatcagc
2401 actggcccca cgcttcaggc acgaaggagg cagtctgtcc tgaacctgat gacacactca
2461 gttaaccaag gtcagaacat tcaccgaaag acaacagcat ccacacgaaa agtgtcactg
2521 gccccctcagg caaacttgac tgaactggat atatattcaa gaaggttatc tcaagaaact
2581 ggcttggaaa taagtgaaga aattaacgaa gaagacttaa aggagtgctt ifitgatgat
2641 atggagagca taccagcagt gactacatgg aacacatacc ttcgatatat tactgtccac
2701 aagagcttaa tttttgtgct aatttggtgc ttagtaattt ttctggcaga ggtggctgct
2761 tctttggttg tgctgtggct ccttggaaac actcctcttc aagacaaagg gaatagtact
2821 catagtagaa ataacagcta tgcagtgatt atcaccagca ccagttcgta ttatgtgttt
2881 tacatttacg tgggagtagc cgacactttg cttgctatgg gattcttcag aggtctacca
2941 ctggtgcata ctcaatcac agtgtcgaaa attttacacc acaaaatgtt acattctgtt
3001 cttcaagcac ctatgtcaac cctcaacacg ttgaaagcag gtgggattct taatagattc
3061 tccaaagata tagcaatttt ggatgacctt ctgcctctta ccatatttga cttcatccag
3121 ttgttattaa ttgtgattgg agctatagca gttgtcgcag ttttacaacc ctacatcttt
3181 gttgcaacag tgccagtgat agtggctttt attatgttga gagcatattt cctccaaacc
3241 tcacagcaac tcaaacaact ggaatctgaa ggcaggagtc caattttcac tcatcttgtt
3301 acaagcttaa aaggactatg gacacttcgt gccttcggac ggcagcctta ctttgaaact
3361 ctgttccaca aagctctgaa tttacatact gccaactggt tcttgtacct gtcaacactg
3421 cgctggttcc aaatgagaat agaaatgatt tttgtcatct tcttcattgc tgttaccttc
3481 atttccattt taacaacagg agaaggagaa ggaagagttg gtattatcct gactttagcc
3541 atgaatatca tgagtacatt gcagtgggct gtaaactcca gcatagatgt ggatagcttg
3601 atgcgatctg tgagccgagt ctttaagttc attgacatgc aacagaagg taaacctacc
3661 aagtcaacca aaccatacaa gaatggccaa ctctcgaaag ttatgattat tgagaattca
3721 cacgtgaaga aagatgacat ctggcccctca gggggccaaa tgactgtcaa agatctcaca
3781 gcaaaataca cagaaggtgg aaatgccata ttagagaaca tttccttctc aataagtcct
3841 ggccagaggg tgggcctctt gggaagaact ggatcaggga agagtacttt gttatcagct
3901 ttttgagac tactgaacac tgaaggagaa atccagatcg atggtgtgtc ttgggattca
```

-continued

```
3961 ataactttgc aacagtggag gaaagccttt ggagtgatac cacagaaagt atttattttt
4021 tctggaacat ttagaaaaaa cttggatccc tatgaacagt ggagtgatca agaaatatgg
4081 aaagttgcag atgaggttgg gctcagatct gtgatagaac agtttcctgg gaagcttgac
4141 tttgtccttg tggatggggg ctgtgtccta agccatggcc acaagcagtt gatgtgcttg
4201 gctagatctg ttctcagtaa ggcgaagatc ttgctgcttg atgaacccag tgctcatttg
4261 gatccagtaa cataccaaat aattagaaga actctaaaac aagcatttgc tgattgcaca
4321 gtaattctct gtgaacacag gatagaagca atgctggaat gccaacaatt tttggtcata
4381 gaagagaaca aagtgcggca gtacgattcc atccagaaac tgctgaacga gaggagcctc
4441 ttccggcaag ccatcagccc ctccgacagg gtgaagctct ttccccaccg gaactcaagc
4501 aagtgcaagt ctaagcccca gattgctgct ctgaaagagg agacagaaga agaggtgcaa
4561 gatacaaggc tttagagagc agcataaatg ttgacatggg acatttgctc atggaattgg
4621 agctcgtggg acagtcacct catggaattg gagctcgtgg aacagttacc tctgcctcag
4681 aaaacaagga tgaattaagt tttttttaa aaaagaaaca tttggtaagg ggaattgagg
4741 acactgatat gggtcttgat aaatggcttc ctggcaatag tcaaattgtg tgaaaggtac
4801 ttcaaatcct tgaagattta ccacttgtgt tttgcaagcc agattttcct gaaaaccctt
4861 gccatgtgct agtaattgga aaggcagctc taaatgtcaa tcagcctagt tgatcagctt
4921 attgtctagt gaaactcgtt aatttgtagt gttggagaag aactgaaatc atacttctta
4981 gggttatgat taagtaatga taactggaaa cttcagcggt ttatataagc ttgtattcct
5041 ttttctctcc tctccccatg atgtttagaa acacaactat attgtttgct aagcattcca
5101 actatctcat ttccaagcaa gtattagaat accacaggaa ccacaagact gcacatcaaa
5161 atatgcccca ttcaacatct agtgagcagt caggaaagag aacttccaga tcctggaaat
5221 cagggttagt attgtccagg tctaccaaaa atctcaatat ttcagataat cacaatacat
5281 cccttacctg ggaaagggct gttataatct ttcacagggg acaggatggt tcccttgatg
5341 aagaagttga tatgcctttt cccaactcca gaaagtgaca agctcacaga cctttgaact
5401 agagtttagc tggaaaagta tgttagtgca aattgtcaca ggacagccct tcificcaca
5461 gaagctccag gtagagggtg tgtaagtaga taggccatgg gcactgtggg tagacacaca
5521 tgaagtccaa gcatttagat gtataggttg atggtggtat gttttcaggc tagatgtatg
5581 tacttcatgc tgtctacact aagagagaat gagagacaca ctgaagaagc accaatcatg
5641 aattagtttt tatatgcttct gttttataat tttgtgaagc aaaattifit ctctaggaaa
5701 tatttatttt aataatgttt caaacatata taacaatgct gtattttaaa agaatgatta
5761 tgaattacat ttgtataaaa taaffittat atttgaaata ttgactttt atggcactag
5821 tatttctatg aaatattatg ttaaaactgg gacaggggag aacctagggt gatattaacc
5881 aggggccatg aatcacctt tggtctggag ggaagccttg gggctgatgc agttgttgcc
5941 cacagctgta tgattcccag ccagcacagc ctcttagatg cagttctgaa gaagatggta
6001 ccaccagtct gactgificc atcaagggta cactgccttc tcaactccaa actgactctt
6061 aagaagactg cattatattt attactgtaa gaaaatatca cttgtcaata aaatccatac
6121 atttgtgtga aa
```

As used herein, the term "gene" has its general meaning in the art and refers to means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed.

As used herein the "allele" has its general meaning in the art and refers to an alternative form of a gene (one member of a pair) that is located at a specific position on a specific chromosome which, when translated result in functional or dysfunctional (including non-existent) gene products.

As used herein, the term "mutation" has its general meaning in the art and refers to any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Mutations include deletion, insertion or substitution of one or more nucleotides. The mutation may occur in the coding region of a gene (i.e. in exons), in introns, or in the regulatory regions (e.g. enhancers, response elements, suppressors, signal sequences, polyadenylation sequences, promoters) of the gene. Generally a mutation is identified in a subject by comparing the sequence of a nucleic acid or polypeptide expressed by said subject with the corresponding nucleic acid or polypeptide expressed in a control population. Where the mutation is within the gene coding sequence, the mutation may be a "missense" mutation, where it replaces one amino acid with another in the gene product, or a "non sense" mutation, where it replaces an amino acid codon with a stop codon. A mutation may also occur in a splicing site where it creates or destroys signals for exon-intron splicing and thereby lead to a gene product of altered structure. A mutation in the genetic material may also be "silent", i.e. the mutation does not result in an alteration of the amino acid sequence of the expression product. In the context of the instant application, mutations identified in CFTR gene or protein are designated pursuant to the nomenclature of Dunnen and Antonarakis (2000). For instance, ">" indicates a substitution at DNA level; "_" (underscore) indicates a range of affected residues, separating the first and last residue affected; "del" indicates a deletion, "dup" indicates a duplication; "ins" indicates a insertion, "inv" indicates an inversion and "con" indicates a conversion. More particularly, "X" denotes that an amino acid is changed to a stop codon (X).

As used herein, the term "homozygous" refers to an individual possessing two copies of the same allele. As used herein, the term "homozygous mutant" refers to an individual possessing two copies of the same allele, such allele being characterized as the mutant form of a gene.

As used herein, the term "heterozygous" refers to an individual possessing two different alleles of the same gene, i.e. an individual possessing two different copies of an allele, such alleles are characterized as mutant forms of a gene.

In some embodiments, the subject harbors at least one mutation in the CFTR gene. The CFTR gene mutations were classified into five classes (sometimes six) according to their resulting damaging effect on the protein. The class I mutations contribute to the formation of proteins with incomplete length and usually involve the complete loss of its activity (e.g. W1282X, 1717-1G→A, G542X, R553X, 2183AA>G). Mutation in the class II lead to abnormal maturation of proteins in the endoplasmic reticulum and Golgi apparatus. The effect of these mutations is premature degradation of the protein. Hence, CFTR does not reach the cell membrane where it should perform its function (e.g. F508del, 2184delA). The gene product having mutations of class III is properly synthesized, transported and incorporated into the cell membrane, but has decreased activity caused by abnormal regulation of the protein. These mutations are frequently situated within one of the nucleotide binding domain. (eg. G551D, R560T). Mutations of class IV cause anomalies in the structure of the transmembrane protein and thereby reduce the conduction of chloride channel (e.g. R117H, R334W). Mutations altering the stability of mRNA represent a class V of the mutations of the CFTR gene (e.g. 2789+5G→A, A455E) (Harriet C., Kristin E. T., Olivier T., et al. Translating the genetics of cystic fibrosis to personalized medicine. Transl Res 2016; 168 40-49).

Examples of CFTR mutations include, but are not limited to 124del23 bp CFTR, CFTRdele1 CFTR, M1V CFTR, Q2X CFT, S4X CFTR, P5L CFTR, S13F CFTR, L15P CFTR, 182delT CFTR, CFTRdele2 CFTR, CFTRdele2-4 CFTR, 185+1G→T CFTR, CFTRdele2,3 CFTR, W19X CFTR, G27R CFTR, G27X CFTR, Q30X CFTR, R31C CFTR, R31L CFTR, Q39X CFTR, A46D CFTR, 296+1G→A CFTR, 296+1G→T CFTR, CFTRdele3-10,14b-16 CFTR, 296+28A→G CFTR, 296+2T→C CFTR, 296+3insT CFTR, 297-3C→T CFTR, 297-1G→A CFTR, E56K CFTR, W57G CFTR, W57X CFTR, 306insA CFTR, 306delTAGA CFTR, E60X CFTR, P67L CFTR, R74W CFTR, R75X CFTR, R75Q CFTR, 365-366insT CFTR, G85E CFTR, 394delTT CFTR, L88X CFTR, G91R CFTR, CFTRdele4-7 CFTR, CFTRdele4-11 CFTR, CFTR50kbdel CFTR, 405+1G→A CFTR, 405+3A→C CFTR, 406-2A→G CFTR, 406-1G→A CFTR, E92K CFTR, E92X CFTR, Q98X CFTR, Q98R CFTR, P99L CFTR, L102R CFTR, 442delA CFTR, 444delA CFTR, 457TAT→G CFTR, D110H CFTR, D110E CFTR, R117C CFTR, R117G CFTR, R117H CFTR, R117H; 5T CFTR, R117H; 7T CFTR, 541delC CFTR, L138ins CFTR, H139R CFTR, 574delA CFTR, I148T CFTR, 602del14 CFTR, Y161D CFTR, 621+1G→T CFTR, 621+3A→G CFTR, L165S CFTR, R170H CFTR, 663delT CFTR, G178R CFTR, 675del4 CFTR, E193X CFTR, 711+1G→T CFTR, 711+3A→G CFTR, 711+5G→A CFTR, 712-1G→T CFTR, H199Y CFTR, V201M CFTR, P205S CFTR, L206W CFTR, W216X CFTR, Q220X CFTR, L227R CFTR, V232D CFTR, 849delG CFTR, 852del22 CFTR, CFTRdup6b-10 CFTR, M265R CFTR, 935delA CFTR, Y275X CFTR, C276X CFTR, 977insA CFTR, 991del5 CFTR, F311L CFTR, 1078delT CFTR, L320V CFTR, 1119delA CFTR, G330X CFTR, R334W CFTR, R334Q CFTR, R334L CFTR, 1138insG CFTR, I336K CFTR, T338I CFTR, S341P CFTR, 1154insTC CFTR, 1161delC CFTR, R347H CFTR, R347P CFTR, A349V CFTR, R352W CFTR, R352Q CFTR, Q359K/T360K CFTR, 1213delT CFTR, 1248+1G→A CFTR, 1249-1G→A CFTR, 1259insA CFTR, 1288insTA CFTR, W401X CFTR, 1341+1G→A CFTR, 5T CFTR, 5T; TG11 CFTR, 5T; TG12 CFTR, 5T; TG13 CFTR, 7T CFTR, 9T CFTR, 1343delG CFTR, Q414X CFTR, 1429del7 CFTR, D443Y CFTR, 1461ins4 CFTR, 1471delA CFTR, L453S CFTR, A455E CFTR, 1497delGG CFTR, V456A CFTR, 1504delG CFTR, 1525-1G→A CFTR, 1525-2A→G CFTR, S466X CFTR, L467P CFTR, M470V CFTR, 1548delG CFTR, E474K CFTR, S489X CFTR, S492F CFTR, 1609delCA CFTR, Q493X CFTR, W496X CFTR, I502T CFTR, I507del CFTR, F508del CFTR, F508C CFTR, D513G CFTR, 1677delTA CFTR, V520F CFTR, C524X CFTR, Q525X CFTR, 1716+1G→A CFTR, CFTRdele11 CFTR, 1717-1G→A CFTR, 1717-8G→A CFTR, G542X CFTR, S549R CFTR, S549N CFTR, G550X CFTR, 1782delA CFTR, G551S CFTR, G551D CFTR, Q552X CFTR, R553X CFTR, 1802delC CFTR, L558S CFTR, A559T CFTR, 1811+1G→C CFTR, R560K CFTR, R560T CFTR, 1811+1G→A CFTR, 1811+1634A→G or 1811+1.6kbA→G CFTR, 1811+1643G→T CFTR, 1812-1G→A CFTR, R560S CFTR, A561E CFTR, V562I CFTR, Y563N CFTR, Y563D CFTR, 1824delA CFTR, 1833delT CFTR, Y569D CFTR, P574H CFTR, F575Y CFTR, G576A CFTR, D579G CFTR, E585X CFTR, E588V CFTR, 1898+1G→A CFTR, 1898+1G→C CFTR, 1898+1G→T CFTR, CFTRdele13,14a CFTR, 1898+3A→G CFTR, 1898+ 5G→T CFTR, 1924del7 CFTR, H609R CFTR, A613T CFTR, D614G CFTR, G622D CFTR, 2055del9→A CFTR, 2075delA CFTR, 2105-2117del13insAGAAA CFTR, 2118del4 CFTR, R668C CFTR, 2143delT CFTR, G673X CFTR, 2183AA→G CFTR, 2184insA CFTR, 2184delA CFTR, 2185insC CFTR, Q685X CFTR, R709X CFTR, K710X CFTR, Q715X CFTR, Q720X CFTR, 2307insA CFTR, L732X CFTR, 2347delG CFTR, 2372del8 CFTR, P750L CFTR, V754M CFTR, R764X CFTR, R785X CFTR, R792X CFTR, 1807M CFTR, 2556insAT CFTR, 2585delT CFTR, 2594delGT CFTR, E822X CFTR, 2622+1G→A CFTR, E831X CFTR, D836Y CFTR, W846X CFTR Y849X CFTR, R851X CFTR, T854T CFTR, 2711delT CFTR, 2721del11 CFTR, 2732insA CFTR, CFTRdele14b-17b CFTR, 2752-26A→G CFTR, W882X CFTR, 2789+2insA CFTR, 2789+5G→A CFTR, 2790-1G→C CFTR, Q890X CFTR, S912X CFTR, S912L CFTR, 2869insG CFTR, Y913X CFTR, 2896insAG CFTR, L927P CFTR, 2942insT CFTR, 2957delT CFTR, S945L CFTR, 2991del32 CFTR, 3007delG CFTR, 3028delA CFTR, L967S CFTR, G970R CFTR, CFTRdele16-17b CFTR, G970D CFTR, S977F CFTR, D979V CFTR, 3120G→A CFTR, CFTRdele17a,17b CFTR, CFTRdele17a-18 CFTR, 3120+1G→A CFTR, 3121-1G→A CFTR, 3121-2A→G CFTR, 3121-977 3499+ 248del2515 CFTR, L997F CFTR, 3132delTG CFTR, A1006E CFTR, 3143del9 CFTR, 3171delC CFTR, 3171insC CFTR, Y1014C CFTR, F1016S CFTR, I1027T CFTR, Y1032C CFTR, Q1042X CFTR, 3271delGG CFTR, 3272-26A→G CFTR, F1052V CFTR, T1053I CFTR, H1054D CFTR, G1061R CFTR, L1065P CFTR, R1066C CFTR, R1066H CFTR, G1069R CFTR, R1070W CFTR, R1070Q CFTR, 3349insT CFTR, F1074L CFTR, L1077P CFTR, W1089X CFTR, Y1092X CFTR, W1098X CFTR, W1098C CFTR, F1099L CFTR, M1101K CFTR, R1102X CFTR, E1104X CFTR, S1118F CFTR, CFTRdele18 CFTR, 3500-2A→G CFTR, W1145X CFTR, D1152H CFTR, V1153E CFTR, 3600G→A CFTR, CFTRdele19 CFTR, CFTRdele19-21 CFTR, 3600+2insT CFTR, 3600+5G→A CFTR, R1158X CFTR, S1159P CFTR, S1159F CFTR, R1162X CFTR, R1162L CFTR, 3659delC CFTR, 3667ins4 CFTR, S1196X CFTR, 3737delA CFTR, W1204X CFTR, 3791delC CFTR, Y122X CFTR, 3821delT CFTR, I1234V CFTR, S1235R CFTR, 3849G→A CFTR, 3849+4A→G CFTR, 3849+5G→A CFTR, 3849+40A→G CFTR, 3849+ 10kbC→T CFTR, 3850-1G→A CFTR, 3850-3T→G CFTR, V1240G CFTR, G1244E CFTR, T1246I CFTR, 3876delA CFTR, 3878delG CFTR, S1251N CFTR, L1254X CFTR, S1255P CFTR, S1255X CFTR, 3905insT CFTR, D1270N CFTR, W1282X CFTR, R1283M CFTR, Q1291R CFTR, 4005+1G→A CFTR, CFTRdele21 CFTR, 4005+2T→C CFTR, 4010del4 CFTR, 4015delA CFTR, 4016insT CFTR, 4022insT CFTR, 4040delA CFTR, N1303K CFTR, Q1313X CFTR, CFTRdele22-24 CFTR, CFTRdele22,23 CFTR, L1324P CFTR, Q1330X CFTR, L1335P CFTR, 4168delCTAAGCC CFTR, G1349D CFTR, 4209TGT-T→AA CFTR, 4218insT CFTR, E1371X CFTR, H1375P CFTR, 4259del5 CFTR, Q1382X CFTR, 4279insA CFTR, 4326delTC CFTR, Q1411X CFTR, Q1412X CFTR, 4374+ 1G→T CFTR, 4374+1G→A CFTR, 4382delA CFTR, 4428insGA CFTR (see, e.g., https://www.cftr2.org/mutations_history, for CFTR mutations).

In one embodiment, the subject harbors at least one allelic mutation selected from class I, class II, class III, class IV or class V.

In one embodiment, the subject harbors at least one mutation selected from class I, class II, class III, class IV or class V in the first allele and at least one mutation selected from class I, class II, class III, class IV or class V in the second allele. In a particular embodiment, the subject harbors at least a mutation of class I in the first allele and at least a mutation of class II in the second allele. In a particular embodiment, the subject harbors at least a mutation of class II in the first allele and at least a mutation of class II in the second allele.

In a particular embodiment, the subject harbors at least one allelic mutation in the CFTR gene including, but not limited to F508del-CFTR, R117H CFTR, G551D CFTR, 2184delA CFTR, or W1282X CFTR.

In one embodiment, the subject harbors at least a F508del mutation in the CFTR gene.

In one embodiment, the subject harbors at least a F508del mutation in the first allele and at least a F508del mutation in the second allele.

In one embodiment, the subject harbors at least a W1282X mutation in the CFTR gene.

In one embodiment, the subject harbors at least a 2184delA mutation in the CFTR gene.

In one embodiment, the subject harbors at least a W1282X mutation in the first allele and at least a 2184delA mutation in the second allele.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein the term "lumacaftor" also called "3-{6-[1-(2,2-difluoro-2H-1,3-benzodioxol-5-yl)cyclopropaneamido]-3-methylpyridin-2-yl}benzoic acid" has its general meaning in the art and refers to the compound characterized by the formula of:

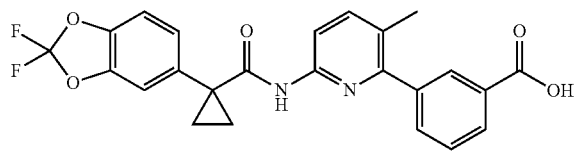 [SMILES: Cc1ccc(NC(=O)C2(c3ccc4c(c3)OC(F)(F)O4)CC2)nc1-c1cccc(C(=O)O)c1]

As used herein the term "ivacaftor" also called "N-(2,4-di-tert-butyl-5-hydroxyphenyl)-4-oxo-1,4-dihydroquinoline-3-carboxamide" has its general meaning in the art and refers to the compound characterized by the formula of:

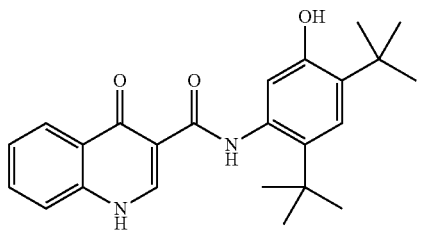 [SMILES: CC(C)(C)c1cc(C(C)(C)C)c(NC(=O)c2c[nH]c3ccccc3c2=O)cc1O]

In some embodiments, the one skilled in the art can easily provide some modifications that will improve the clinical efficacy of the nucleic acid molecule of the present invention. In a particular embodiment, the nucleic acid molecule of the present invention according to the invention is a LNA oligonucleotide. As used herein, the term "LNA" (Locked Nucleic Acid) (or "LNA oligonucleotide") refers to an oligonucleotide containing one or more bicyclic, tricyclic or polycyclic nucleoside analogues also referred to as LNA nucleotides and LNA analogue nucleotides. LNA oligonucleotides, LNA nucleotides and LNA analogue nucleotides are generally described in International Publication No. WO 99/14226 and subsequent applications; International Publication Nos. WO 00/56746, WO 00/56748, WO 00/66604, WO 01/25248, WO 02/28875, WO 02/094250, WO 03/006475; U.S. Pat. Nos. 6,043,060, 6,268,490, 6,770,748, 6,639,051, and U.S. Publication Nos. 2002/0125241, 2003/0105309, 2003/0125241, 2002/0147332, 2004/0244840 and 2005/0203042, all of which are incorporated herein by reference. LNA oligonucleotides and LNA analogue oligonucleotides are commercially available from, for example, Proligo LLC, 6200 Lookout Road, Boulder, Colo. 80301 USA. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the nucleic acid molecule of the present invention also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

As used herein, the term "combination" is intended to refer to all forms of administration that provide a first drug together with a further (second, third . . . ) drug. The drugs may be administered simultaneous, separate or sequential and in any order. According to the invention, the drug is administered to the subject using any suitable method that enables the drug to reach the lungs. In some embodiments, the drug administered to the subject systemically (i.e. via systemic administration). Thus, in some embodiments, the drug is administered to the subject such that it enters the circulatory system and is distributed throughout the body. In some embodiments, the drug is administered to the subject by local administration, for example by local administration to the lungs. In some embodiments, lumacaftor and ivacaftor are administered to the subject in the same pharmaceutical composition. In some embodiments, lumacaftor and ivacaftor are administered in the form of tablets for oral administration. The combination of Lumacaftor/ivacaftor is already commercially available under the brand name Orkambi® in the form of 200 mg of/125 mg tablets (Lumacaftor/Ivacaftor) for the treatment of cystic fibrosis.

In some embodiments, the nucleic acid molecule is delivered by any device adapted to introduce one or more therapeutic compositions into the upper and/or lower respiratory tract.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. One of ordinary skill in the art would be able to determine such amounts based on such factors as the subject's size, the severity of the subject's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drugs of the present invention are administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1. Effect of TSB control, ANO1 TSB, Orkambi® or TSB ANO1+Orkambi® on mucus dynamics. Primary hAECB and fully differentiated human bronchial air-liquid-interface cultures, isolated from bronchial biopsies from CF (F508del/F508del) subjects were transfected with TSB control (control) or ANO1 TSB every day during 3 days and/or stimulated with VX-770 and VX-809 (Orkambi®) for 24 h. The movements of 100 beads were quantified for each condition and the average speed (µm/ms) was determined. Histograms represent the average values±SDs and were compared using ANOVA coupled with Dunnett's, Bonferroni's and Tukey's post-hoc test.

Figure 2:
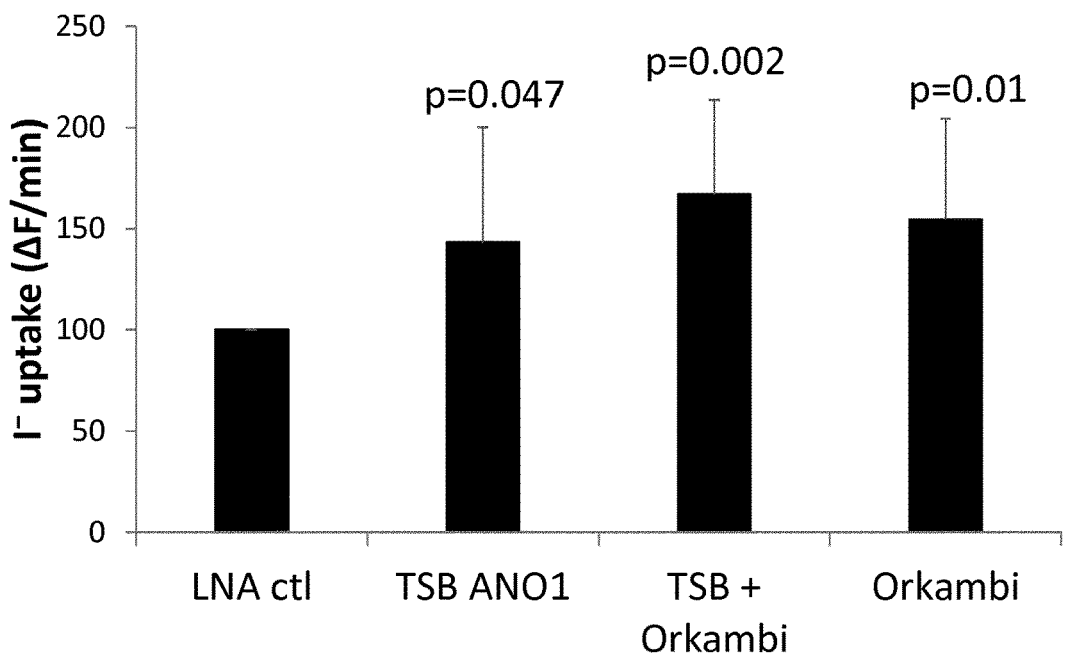

FIG. 2. Effect of TSB control, ANO1 TSB, Orkambi® or TSB ANO1+Orkambi® on chloride channel activity. CFPAC cells were transfected with TSB control (control) or ANO1 TSB for 24 h and/or stimulated with VX-770 and VX-809 (Orkambi®) for 24 h and chloride channel activity assay was assessed. Quantification of global channel activity of CF pancreatic epithelial cells transfected with ANO1 TSB or a negative control and/or stimulated with Orkambi® (n=8, in triplicate). Histograms represent average values±SDs and the conditions were compared using ANOVA coupled with Dunnett's, Bonferroni's and Tukey's post-hoc test.

Figure 3:
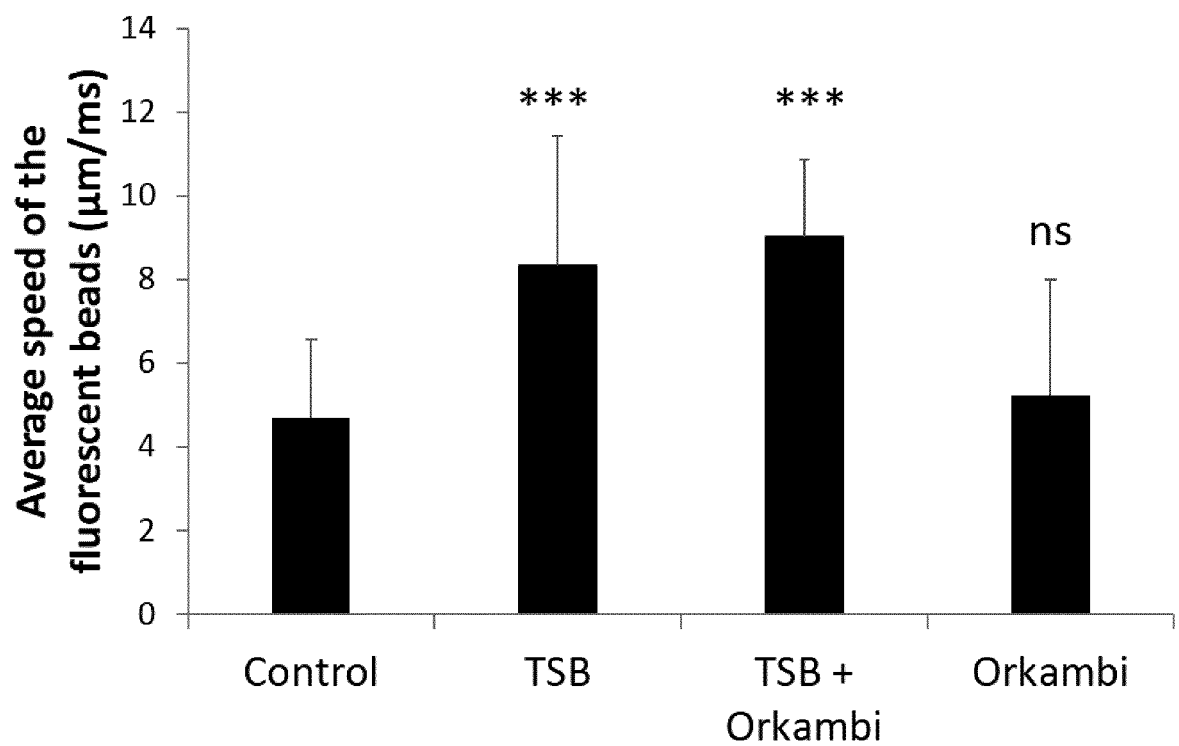

FIG. 3: Effect of TSB control, ANO1 TSB, Orkambi or TSB ANO1+Orkambi on mucus dynamics. Primary hAECB and fully differentiated human bronchial air-liquid-interface cultures, isolated from bronchial biopsies from CF (2184Δa+W1282X) subjects were transfected with TSB control (control) or ANO1 TSB every day during 3 days and/or stimulated with VX-770 and VX-809 (Orkambi) for 24 h. The movements of 100 beads were quantified for each condition and the average speed (µm/ms) was determined. Histograms represent the average values±SDs and were compared using ANOVA coupled with Dunnett's, Bonferroni's and Tukey's post-hoc test FIG. 4: Effect of TSB control, ANO1 TSB, Orkambi or TSB ANO1+Orkambi on mucus dynamics. Primary hAECB and fully differentiated human bronchial air-liquid-interface cultures, isolated from bronchial biopsies from CF (1717-1G>A+F508Del) subjects were transfected with TSB control (control) or ANO1 TSB every day during 3 days and/or stimulated with VX-770 and VX-809 (Orkambi) for 24 h. The movements of 100 beads were quantified for each condition and the average speed (µm/ms) was determined. Histograms represent the average values±SDs and were compared using ANOVA coupled with Dunnett's, Bonferroni's and Tukey's post-hoc test.

Figure 5:
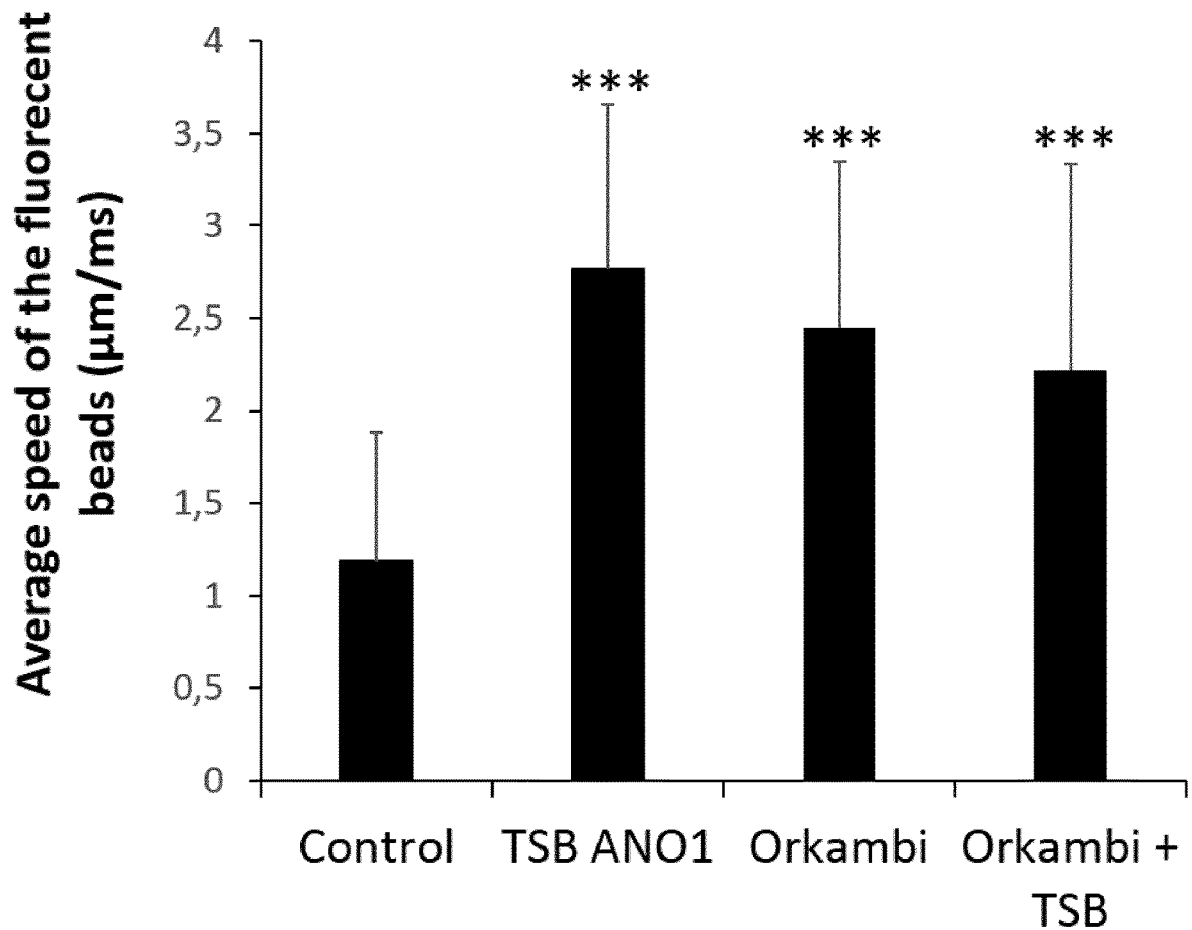

FIG. 5: Effect of TSB control, ANO1 TSB, Orkambi or TSB ANO1+Orkambi on mucus dynamics. Primary hAECB and fully differentiated human bronchial air-liquid-interface cultures, isolated from bronchial biopsies from CF (F508/2183AA>G) subjects were transfected with TSB control (control) or ANO1 TSB every day during 3 days and/or stimulated with VX-770 and VX-809 (Orkambi) for 24 h. The movements of 100 beads were quantified for each condition and the average speed (µm/ms) was determined. Histograms represent the average values±SDs and were compared using ANOVA coupled with Dunnett's, Bonferroni's and Tukey's post-hoc test.

EXAMPLE

Material & Methods

Cell Culture

Primary hAECB isolated from bronchial biopsies from CF (F508del/F508del) subjects were purchased from Epithelix SARL (Geneva, Switzerland). Fully differentiated ALI cultures (MucilAir,™), were cultured according to the provider's recommendations.

CFPAC cell line were provided by Dr. Caroline Norez (STIM, Poitiers, France). This line was derived from a ductal adenocarcinoma (liver metastasis) from a subject with cystic fibrosis. Cells were cultured as recommended by ATCC (www.lgcstandards-atcc.org) in Iscove's Modified Dulbecco's Medium with fetal bovine serum at a final concentration of 10%. Cells were maintained at 37° C. in a humidified atmosphere of air with 5% $CO_2$. All cells were tested for mycoplasma contamination (Lonza, Ambroise, France).

Cell Transfections and Stimulation

CFPAC cells were transfected with LNA-enhanced oligonucleotides targeting the miR-9 target site in the ANO1 3'UTR (ANO1 TSB) or with a miRCURY LNA microRNA inhibitor negative control (TSB control) (Exiqon, Denmark) using Interferin (Polyplus, Ozyme, France). CFPAC cells were stimulated for 24 h with VX-770 (100 nM) and VX-809 (1 µM) (Selleck Chemicals, Houston, USA) [1]. Twenty-four hours after the transfection and/or stimulation, the cells were processed for chloride activity.

hAECB were transfected by adding medium containing LNA control or ANO1 TSB without any transfection reagent to ALI cells. After a 2-h incubation at 37° C., the medium was removed to restore the ALI condition. Freshly prepared LNA control or ANO1 TSB were added every day for three days, and mucus clearance assay was assessed 24 h post-treatment [2].

ANO1, CFTR and Global Chloride Channel Activity Assay

The chloride channel activity was assessed by t quenching of halide-sensitive YFP-H148Q/I152L protein (Thermo Fischer Scientific). The probe was transfected into the cells, and after 48 h of culture, conductance was stimulated for CFTR and ANO1 respectively with cAMP agonist cocktail and UTP (10 µM). For the global chloride channel activity, after 48 h of transfection with the probe, the conductance was stimulated with cAMP agonist cocktail and UTP (10 µM) together. I$^-$ solution (140 mM) was added, and the fluorescence was recorded using a plate reader as previously described [3]. The initial I$^-$ influx rate upon addition of each solution was computed from changes in YFP fluorescence data using non-linear regression. For quantitative analysis, the slope for fluorescence quenching, which correlates to the level of chloride conductance (I$^-$ uptake), was determined using linear regression. The rate of change (ΔF/min) was then calculated.

Mucus Clearance Assay

Thirty days after transfection and stimulation of hAECB cells with control TSB, ANO1 TSB, and/or Orkambi®, FluoSpheres Carboxylate-Modified Microspheres, 1.0 µm, yellow-green fluorescent (505/515) (Thermo Fisher Scientific) diluted in culture medium (1/50) were added to the apical face of the cultures. Movement of the beads was recorded under an Axiovert 200 microscope (Zeiss). Fluorescence images were collected every 3 ms and composed into a time-lapse image series using Axiovision software (version 4.6).

Results

Figure 4:
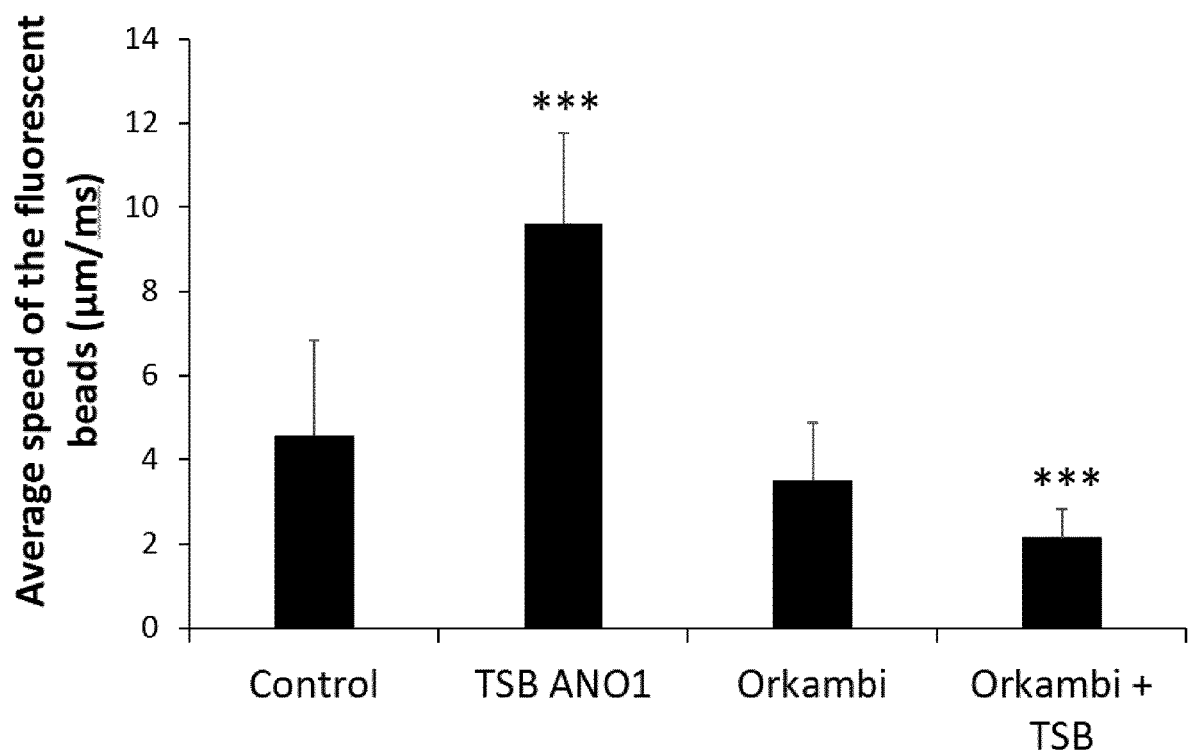

We have instigated the combination of Orkambi® and ANO1 TSB (SEQ ID NO:1). The results are depicted in FIGS. 1, 2, 3, 4 and 5. Thus the combination increases mucociliary clearance (FIG. 1, FIG. 3) and chloride channel activity (FIG. 2). Surprisingly, we have found that the combination is not efficient with certain mutations (FIG. 4 and FIG. 5). Thus the combination of Orkambi® and ANO1 TSB (SEQ ID NO:1) represents an alternative treatment for CF subjects.

REFERENCES

Throughout this application, various references describe the state of the art to which this invention pertains. The disclosures of these references are hereby incorporated by reference into the present disclosure.

1. Matthes E, Goepp J, Carlile G W, et al. Low free drug concentration prevents inhibition of F508del CFTR functional expression by the potentiator VX-770 (ivacaftor). Br J Pharmacol 2016; 173: 459-470.
2. Sonneville F, Ruffin M, Coraux C, et al. MicroRNA-9 downregulates the ANO1 chloride channel and contributes to cystic fibrosis lung pathology. Nature communications 2017; 8: 710.
3. Saint-Criq V, Ruffin M, Rebeyrol C, et al. Azithromycin fails to reduce inflammation in cystic fibrosis airway epithelial cells. Eur J Pharmacol 2012; 674: 1-6.
4. Harriet C., Kristin E. T., Olivier T., et al. Translating the genetics of cystic fibrosis to personalized medicine. Transl Res 2016; 168 40-49.

The invention claimed is:

1. A method of treating cystic fibrosis in a subject in need thereof comprising administering to the subject a therapeutically effective combination of lumacaftor, ivacaftor and a nucleic acid molecule comprising the nucleic acid sequence (SEQ ID NO: 1)
TTTTCTCCGTCTTTGGGACCT.

2. The method of claim 1 wherein the subject harbors at least one allelic mutation selected from class I, class II, class III, class IV or class V.

3. The method of claim 1 wherein the subject harbors at least one mutation selected from class I, class II, class III, class IV or class V in the first allele and at least one mutation selected from class I, class II, class III, class IV or class V in the second allele.

4. The method of claim 3, wherein the subject harbors at least a mutation of class II in the first allele and at least a mutation of class II in the second allele.

5. The method of claim 3 wherein the subject harbors at least a mutation of class I in the first allele and at least a mutation of class II in the second allele.

6. The method of claim 2 wherein the subject harbors at least one allelic mutation selected from F508del-CFTR, R117H CFTR, 2184delA CFTR, W1282X CFTR or G551D CFTR.

7. The method of claim 4 wherein the subject harbors at least a F508del mutation in the first allele and at least a F508del mutation in the second allele.

8. The method of claim 5 wherein the subject harbors at least a W1282X mutation in the first allele and at least a 2184delA mutation in the second allele.

9. The method of claim 1 wherein the nucleic acid molecule comprises LNA nucleotides, or morpholino nucleotides, or 2'-O-methyl modified nucleotides, or 2'-O-methoxyethyl modified nucleotides, or 2'-fluoro modified nucleotides.

10. The method of claim 1 wherein lumacaftor and ivacaftor are administered to the subject in the same pharmaceutical composition.

11. The method of claim 8 wherein lumacaftor and ivacaftor are administered in the form of tablets for oral administration.

12. The method of claim 1 wherein the nucleic acid molecule is delivered by any device adapted to introduce one or more therapeutic compositions into the upper and/or lower respiratory tract.

* * * * *

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial
<220> FEATURE:
<223> OTHER INFORMATION: Synthetic PCR primer for GAPDH - forward
      sequence

<400> SEQUENCE: 1
tgcccagaac atcatccctg                                                   20

<210> SEQ ID NO 2
<211> LENGTH: 20
<212> TYPE: DNA
<213> ORGANISM: Artificial
<220> FEATURE:
<223> OTHER INFORMATION: Synthetic PCR primer for GAPDH - reverse
      sequence

<400> SEQUENCE: 2
tcagatccac gacggacaca                                                   20

<210> SEQ ID NO 3
<211> LENGTH: 20
<212> TYPE: DNA
<213> ORGANISM: Artificial
<220> FEATURE:
<223> OTHER INFORMATION: Synthetic PCR primer for ARP2 - forward
      sequence

<400> SEQUENCE: 3
cacatcttcc cagctttggt                                                   20

<210> SEQ ID NO 4
<211> LENGTH: 20
<212> TYPE: DNA
<213> ORGANISM: Artificial
<220> FEATURE:
<223> OTHER INFORMATION: Synthetic PCR primer for ARP2 - reverse
      sequence

<400> SEQUENCE: 4
cagctcactt gcctcatcac                                                   20

<210> SEQ ID NO 5
<211> LENGTH: 20
```

```
<212> TYPE: DNA
<213> ORGANISM: Artificial
<220> FEATURE:
<223> OTHER INFORMATION: Synthetic PCR primer for ARP3 -
      forward sequence

<400> SEQUENCE: 5
caggctgttc ttgccttagc                                              20

<210> SEQ ID NO 6
<211> LENGTH: 20
<212> TYPE: DNA
<213> ORGANISM: Artificial
<220> FEATURE:
<223> OTHER INFORMATION: Synthetic PCR primer for ARP3 - reverse
      sequence

<400> SEQUENCE: 6
atccttcagc cacaggaatg                                              20

<210> SEQ ID NO 7
<211> LENGTH: 20
<212> TYPE: DNA
<213> ORGANISM: Artificial
<220> FEATURE:
<223> OTHER INFORMATION: Synthetic PCR primer for ARPC1a- forward
      sequence

<400> SEQUENCE: 7
gaggattaac cgtgcagcca                                              20

<210> SEQ ID NO 8
<211> LENGTH: 20
<212> TYPE: DNA
<213> ORGANISM: Artificial
<220> FEATURE:
<223> OTHER INFORMATION: Synthetic PCR primer for ARPC1a- reverse
      sequence

<400> SEQUENCE: 8
cttgctcacc caccagtcat                                              20

<210> SEQ ID NO 9
<211> LENGTH: 20
<212> TYPE: DNA
<213> ORGANISM: Artificial
<220> FEATURE:
<223> OTHER INFORMATION: Synthetic PCR primer for ARPC2- forward
      sequence

<400> SEQUENCE: 9
caccgccctt gtttctcctt                                              20

<210> SEQ ID NO 10
<211> LENGTH: 20
<212> TYPE: DNA
<213> ORGANISM: Artificial
<220> FEATURE:
<223> OTHER INFORMATION: Synthetic PCR primer for ARPC2- reverse
      sequence

<400> SEQUENCE: 10
gcttctggtt tgtttccggc                                              20

<210> SEQ ID NO 11
<211> LENGTH: 20
<212> TYPE: DNA
```

```
<213> ORGANISM: Artificial
<220> FEATURE:
<223> OTHER INFORMATION: Synthetic PCR primer for ARPC3- forward
      sequence

<400> SEQUENCE: 11
ccatttatgc caagcctgcg                                                   20

<210> SEQ ID NO 12
<211> LENGTH: 20
<212> TYPE: DNA
<213> ORGANISM: Artificial
<220> FEATURE:
<223> OTHER INFORMATION: Synthetic PCR primer for ARPC3- reverse
      sequence

<400> SEQUENCE: 12
gtccaccact tgctgggttt                                                   20

<210> SEQ ID NO 13
<211> LENGTH: 20
<212> TYPE: DNA
<213> ORGANISM: Artificial
<220> FEATURE:
<223> OTHER INFORMATION: Synthetic PCR primer for ARPC4- forward
      sequence

<400> SEQUENCE: 13
ctctccgccc ctaccttagt                                                   20

<210> SEQ ID NO 14
<211> LENGTH: 20
<212> TYPE: DNA
<213> ORGANISM: Artificial
<220> FEATURE:
<223> OTHER INFORMATION: Synthetic PCR primer for ARPC4- reverse
      sequence

<400> SEQUENCE: 14
tgctactcct gacttcgacc                                                   20

<210> SEQ ID NO 15
<211> LENGTH: 20
<212> TYPE: DNA
<213> ORGANISM: Artificial
<220> FEATURE:
<223> OTHER INFORMATION: Synthetic PCR primer for ARPC5- forward
      sequence

<400> SEQUENCE: 15
gaaggtggac gtggacgaat                                                   20

<210> SEQ ID NO 16
<211> LENGTH: 20
<212> TYPE: DNA
<213> ORGANISM: Artificial
<220> FEATURE:
<223> OTHER INFORMATION: Synthetic PCR primer for ARPC5- reverse
      sequence

<400> SEQUENCE: 16
gctgtcatgt ttccttgccg                                                   20

<210> SEQ ID NO 17
<211> LENGTH: 21
<212> TYPE: DNA
<213> ORGANISM: Artificial
```

```
<220> FEATURE:
<223> OTHER INFORMATION: Synthetic PCR primer for Col1a1- forward
      sequence

<400> SEQUENCE: 17
ccagtggcgg ttatgacttc a                                              21

<210> SEQ ID NO 18
<211> LENGTH: 21
<212> TYPE: DNA
<213> ORGANISM: Artificial
<220> FEATURE:
<223> OTHER INFORMATION: Synthetic PCR primer for Col1a1- reverse
      sequence

<400> SEQUENCE: 18
gctgcggatg ttctcaatct g                                              21

<210> SEQ ID NO 19
<211> LENGTH: 20
<212> TYPE: DNA
<213> ORGANISM: Artificial
<220> FEATURE:
<223> OTHER INFORMATION: Synthetic PCR primer for Lox - forward sequence

<400> SEQUENCE: 19
agggcggatg tcagagacta                                                20

<210> SEQ ID NO 20
<211> LENGTH: 20
<212> TYPE: DNA
<213> ORGANISM: Artificial
<220> FEATURE:
<223> OTHER INFORMATION: Synthetic PCR primer for Lox - reverse sequence

<400> SEQUENCE: 20
aatccctgtg tgtgtgcagt                                                20

<210> SEQ ID NO 21
<211> LENGTH: 17
<212> TYPE: DNA
<213> ORGANISM: Artificial
<220> FEATURE:
<223> OTHER INFORMATION: Synthetic PCR primer for Loxl2 - forward
      sequence

<400> SEQUENCE: 21
cctccctccc gctttca                                                   17

<210> SEQ ID NO 22
<211> LENGTH: 21
<212> TYPE: DNA
<213> ORGANISM: Artificial
<220> FEATURE:
<223> OTHER INFORMATION: Synthetic PCR primer for Loxl2 - reverse
      sequence

<400> SEQUENCE: 22
caagtgtgca gtcctgggtt t                                              21

<210> SEQ ID NO 23
<211> LENGTH: 20
<212> TYPE: DNA
<213> ORGANISM: Artificial
<220> FEATURE:
<223> OTHER INFORMATION: Synthetic PCR primer for Tg2 - forward sequence
```

<400> SEQUENCE: 23
ggaggagcga cgggaatatg				20

<210> SEQ ID NO 24
<211> LENGTH: 20
<212> TYPE: DNA
<213> ORGANISM: Artificial
<220> FEATURE:
<223> OTHER INFORMATION: Synthetic PCR primer for Tg2 - reverse sequence

<400> SEQUENCE: 24
attccatcct cgaactgccc				20

<210> SEQ ID NO 25
<211> LENGTH: 20
<212> TYPE: DNA
<213> ORGANISM: Artificial Sequence
<220> FEATURE:
<223> OTHER INFORMATION: Synthetic PCR primer for Col1a2 - forward
      sequence

<400> SEQUENCE: 25
ctgatggcag agctggtgta				20

<210> SEQ ID NO 26
<211> LENGTH: 20
<212> TYPE: DNA
<213> ORGANISM: Artificial Sequence
<220> FEATURE:
<223> OTHER INFORMATION: Synthetic PCR primer for Col1a2 - reverse
      sequence

<400> SEQUENCE: 26
atgttgccag cttcacctct				20

<210> SEQ ID NO 27
<211> LENGTH: 18
<212> TYPE: DNA
<213> ORGANISM: Artificial Sequence
<220> FEATURE:
<223> OTHER INFORMATION: Synthetic PCR primer for UBC - forward sequence

<400> SEQUENCE: 27
cagttggtcc tgcgcttg				18

<210> SEQ ID NO 28
<211> LENGTH: 23
<212> TYPE: DNA
<213> ORGANISM: Artificial Sequence
<220> FEATURE:
<223> OTHER INFORMATION: Synthetic PCR primer for UBC - reverse sequence

<400> SEQUENCE: 28 tttttggga atgcaacaac ttt				23

<210> SEQ ID NO 29
<211> LENGTH: 20
<212> TYPE: DNA
<213> ORGANISM: Artificial Sequence
<220> FEATURE:
<223> OTHER INFORMATION: Synthetic PCR primer for ARPC2 - forward
      sequence

<400> SEQUENCE: 29
tttcatcccg ctaatcttgg				20

<210> SEQ ID NO 30
<211> LENGTH: 20
<212> TYPE: DNA
<213> ORGANISM: Artificial Sequence
<220> FEATURE:
<223> OTHER INFORMATION: Synthetic PCR primer for ARPC2 - reverse sequence

<400> SEQUENCE: 30
gggagaaaag ggaagtgagg                                            20

<210> SEQ ID NO 31
<211> LENGTH: 18
<212> TYPE: DNA
<213> ORGANISM: Artificial Sequence
<220> FEATURE:
<223> OTHER INFORMATION: Synthetic PCR primer for ACTA2 - forward sequence

<400> SEQUENCE: 31
gaagagcatc ccaccctg                                              18

<210> SEQ ID NO 32
<211> LENGTH: 18
<212> TYPE: DNA
<213> ORGANISM: Artificial Sequence
<220> FEATURE:
<223> OTHER INFORMATION: Synthetic PCR primer for ACTA2 - reverse sequence

<400> SEQUENCE: 32
attttctccc ggttggcc                                              18

<210> SEQ ID NO 33
<211> LENGTH: 22
<212> TYPE: DNA
<213> ORGANISM: Artificial Sequence
<220> FEATURE:
<223> OTHER INFORMATION: Synthetic PCR primer for COL1A1 - forward sequence

<400> SEQUENCE: 33
ttgagactca gccacccaga gt                                         22

<210> SEQ ID NO 34
<211> LENGTH: 21
<212> TYPE: DNA
<213> ORGANISM: Artificial Sequence
<220> FEATURE:
<223> OTHER INFORMATION: Synthetic PCR primer for COL1A1 - reverse sequence

<400> SEQUENCE: 34
cagttcttgg ctgggtgttt t                                          21

<210> SEQ ID NO 35
<211> LENGTH: 20
<212> TYPE: DNA
<213> ORGANISM: Artificial Sequence
<220> FEATURE:
<223> OTHER INFORMATION: Synthetic PCR primer for COL1A2 - forward sequence

<400> SEQUENCE: 35
agcaggtcct tggaaacctt                                            20

```
<210> SEQ ID NO 36
<211> LENGTH: 20
<212> TYPE: DNA
<213> ORGANISM: Artificial Sequence
<220> FEATURE:
<223> OTHER INFORMATION: Synthetic PCR primer for COL1A2 - reverse
      sequence

<400> SEQUENCE: 36
gaaaaggagt tggacttggc                                              20
```